(12) United States Patent
Wong et al.

(10) Patent No.: US 12,144,682 B2
(45) Date of Patent: Nov. 19, 2024

(54) AUTOMATION-ASSISTED VENOUS CONGESTION ASSESSMENT IN POINT OF CARE ULTRASOUND

(71) Applicant: EchoNous, Inc., Redmond, WA (US)

(72) Inventors: Eric Wong, Redmond, WA (US); Babajide Ayinde, Redmond, WA (US); Philippe Rola, Redmond, WA (US)

(73) Assignee: Echonous, Inc., Redmond, WA (US)

( * ) Notice: Subject to any disclaimer, the term of this patent is extended or adjusted under 35 U.S.C. 154(b) by 85 days.

(21) Appl. No.: 17/868,577

(22) Filed: Jul. 19, 2022

(65) Prior Publication Data

US 2024/0023937 A1   Jan. 25, 2024

(51) Int. Cl.
*A61B 8/00* (2006.01)
*A61B 8/06* (2006.01)
*A61B 8/08* (2006.01)

(52) U.S. Cl.
CPC .............. *A61B 8/46* (2013.01); *A61B 8/06* (2013.01); *A61B 8/52* (2013.01); *A61B 8/463* (2013.01)

(58) Field of Classification Search
CPC .... A61B 8/46; A61B 8/06; A61B 8/52; A61B 8/463
See application file for complete search history.

(56) References Cited

U.S. PATENT DOCUMENTS

| 2019/0323895 | A1* | 10/2019 | Kostopoulos | ......... G01J 5/0265 |
| 2019/0336107 | A1* | 11/2019 | Hope Simpson | ... G01S 15/8977 |
| 2019/0377978 | A1 | 12/2019 | Rao et al. | |
| 2020/0022670 | A1* | 1/2020 | Eibl | ...................... A61B 8/4488 |
| 2020/0175652 | A1 | 6/2020 | Agarwal et al. | |
| 2021/0267569 | A1* | 9/2021 | Yamamoto | ................ A61B 8/06 |
| 2021/0345986 | A1* | 11/2021 | Cook | ..................... G06T 7/0012 |
| 2022/0031288 | A1* | 2/2022 | Yamamoto | ............. A61B 8/488 |
| 2022/0061810 | A1* | 3/2022 | Dickie | ..................... A61B 8/463 |
| 2023/0011489 | A1* | 1/2023 | Amans | .................... A61B 5/128 |
| 2023/0058450 | A1* | 2/2023 | Lee | ........................ A61B 8/5223 |
| 2023/0062672 | A1* | 3/2023 | Hyun | ..................... A61B 8/5207 |

FOREIGN PATENT DOCUMENTS

| KR | 20210016860 A | 2/2021 |
| KR | 20210118285 A | 9/2021 |
| KR | 20220082137 A | 6/2022 |

OTHER PUBLICATIONS

William et al. ; "Quantifying systemic congestion with Point-Of-Care ultrasound: development of the venous excess ultrasound grading system"; The ultrasound Journal; pp. 1-12 (2020).*

* cited by examiner

*Primary Examiner* — Dixomara Vargas
(74) *Attorney, Agent, or Firm* — Seed Intellectual Property Law Group LLP

(57) ABSTRACT

A diagnostic facility is described. The facility accesses a set of trained machine learning models. For each of a plurality of stages of a diagnostic ultrasound protocol for blood vessels, the facility causes an ultrasound device to capture from the person an ultrasound artifact of a type specified for the stage that features a blood vessel specified for the stage; applies one of the trained machine learning models to the captured ultrasound artifact to produce a prediction; and determines a score for the stage based at least in part on the produced prediction. The facility combines the determined scores to produce a diagnosis grade for the person.

29 Claims, 11 Drawing Sheets
(6 of 11 Drawing Sheet(s) Filed in Color)

AUTOMATION-ASSISTED VENOUS CONGESTION ASSESSMENT IN POINT OF CARE ULTRASOUND

BACKGROUND

Ultrasound imaging is a useful medical imaging modality. For example, internal structures of a patient's body may be imaged before, during or after a therapeutic intervention. Also, qualitative and quantitative observations in an ultrasound image can be a basis for diagnosis. For example, ventricular volume determined via ultrasound is a basis for diagnosing, for example, ventricular systolic dysfunction and diastolic heart failure.

A healthcare professional typically holds a portable ultrasound probe, sometimes called a "transducer," in proximity to the patient and moves the transducer as appropriate to visualize one or more target structures in a region of interest in the patient. A transducer may be placed on the surface of the body or, in some procedures, a transducer is inserted inside the patient's body. The healthcare professional coordinates the movement of the transducer so as to obtain a desired presentation on a screen, such as a two-dimensional cross-section of a three-dimensional volume.

Particular views of an organ or other tissue or body feature (such as fluids, bones, joints or the like) can be clinically significant. Such views may be prescribed by clinical standards as views that should be captured by the ultrasound operator, depending on the target organ, diagnostic purpose or the like.

Clinical diagnostic protocols specify a way of collecting and analyzing information about a patient to determine a likely diagnosis of a medical issue. Some such protocols specify ways of collecting ultrasound images and/or videos from particular views; identifying certain visual features in this ultrasound data; and measuring or otherwise assessing those visual features.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION

Figure 1:
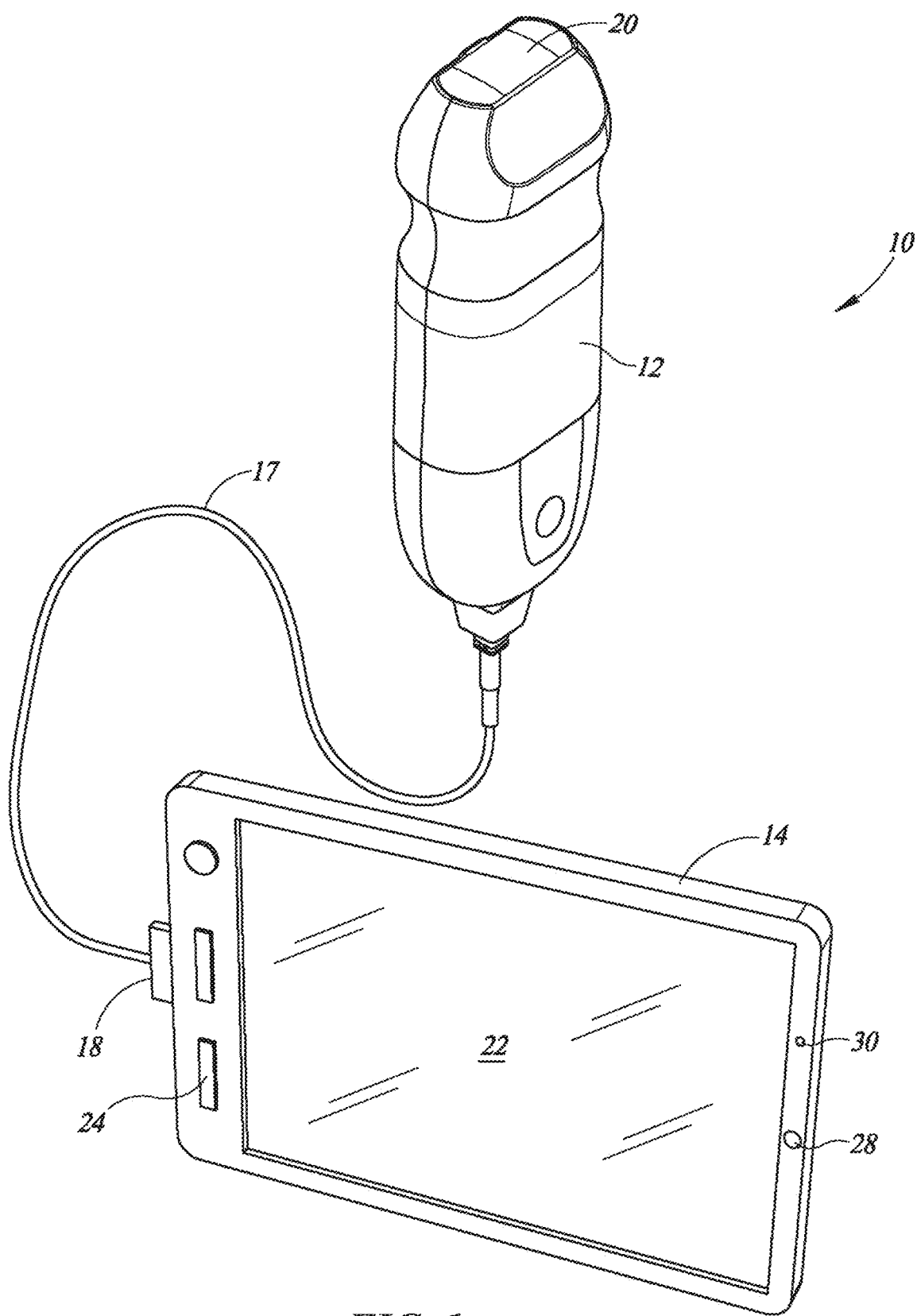
FIG. 1 is a schematic illustration of a physiological sensing device 10, in accordance with one or more embodiments of the present disclosure.

One ultrasound diagnostic protocol is the Venous Excess Ultrasound ("VExUS") Grading System, designed to assess venous congestion, and aid in the evaluation of hemodynamic pathologies and underlying acute kidney injury. The following resources contain details about VExUS, each of which is hereby incorporated by reference in its entirety: (1) Beaubien-Souligny et al., Quantifying systemic congestion with Point-Of-Care ultrasound: development of the venous excess ultrasound grading system, Ultrasound J 12:16 (2020), available at doi.org/10.1186/s13089-020-00163-w; (2) Rola et al., Clinical applications of the venous excess ultrasound (VExUS) score: conceptual review and case series, Ultrasound J 13:32 (2021), available at doi.org/10.1186/s13089-021-00232-8; (3) Additional materials: Quantifying systemic congestion with Point-Of-Care ultrasound: Development of the Venous EXcess UltraSound (VEXUS) score, available at static-content.springer.com/esm/art%3A10.1186%2Fs13089-020-00163-w/MediaObjects/13089_2020_163_MOESM1_ESM.docx; and (4) Wiskar, WesternSono, Solid Organ Doppler Assessment of Venous Congestion, available at www.youtube.com/watch?v=e_blVvFV6jE. In cases where particular contents of a patent, patent application, or other document incorporated herein by reference conflict with the present patent application, the present patent application controls. VExUS involves the acquisition and analysis of four ultrasound artifacts, each said to correspond to a "stage" of the protocol: structure of the inferior vena cava ("IVC"); and continuous-wave ("CW") Doppler patterns showing blood flow in the hepatic vein ("HV"), the portal vein ("PV"), and the intrarenal veins ("IRVs").

The inventors have recognized that it is difficult and time-consuming for clinicians to learn to effectively capture these ultrasound artifacts, analyze them, and determine a patient's VExUS score based on the results of the analysis. The inventors have further recognized that this process can be error-prone, even for clinicians having significant experience performing it. Also, may clinicians may fail to recognize such errors—such as capturing and using images that are not of sufficient quality—enabling them to propagate into inaccurate protocol results.

In response, the inventors have conceived and reduced to practice a software and/or hardware facility that automatically performs VExUS and other similar ultrasound diagnostic protocols for a patient ("the facility"). In particular, for each of the four stages of the protocol, the facility establishes ultrasound settings suitable for the stage; directs the operator to capture the ultrasound artifact specified for the stage; applies one or more machine learning models to assess the quality level of the captured artifact and/or interpret the contents of the artifact; and scores the stage based on the interpretation as a basis for calculating an overall protocol grade for the patient.

In some embodiments, for the protocol's first stage, the facility directs the operator to capture an ultrasound image of the patient's IVC. The facility applies a trained image grading machine learning model to assess the quality of the image based on the ability to locate in the image the IVC walls, and determine the IVC orientation; if the assessed quality level of the image is assessed to be inadequate, the facility directs the operator to capture a new IVC image. Otherwise, the facility applies a trained machine learning model—such as a keypoint detection model or a segmentation model—to measure the inner diameter of the IVC at a position along the length of the IVC specified by the protocol. In some embodiments, the facility performs this process with respect to an ultrasound image showing the IVC in long axis view, an ultrasound image showing the IVC in short axis view, or both. If the measured length is less than a threshold length specified by the protocol, then the facility assigns a first protocol grade indicating no or minimal venous congestion, else the facility continues.

In some embodiments, for each of the protocol's second through fourth stages, the facility goes on to direct the operator to capture an image of the patient's HV, PV, or IRVs. The facility applies to the image an image grading model, and, if its quality level is assessed to be adequate, an object detection model to localize the center of the blood vessel. The facility establishes a Doppler region of interest ("ROI") over that localized center, and initiates Doppler CW blood flow pattern capture. In some embodiments, the facility displays the captured blood flow pattern and scoring criteria specified for the stage by the protocol, and directs the operator to assign a score to the blood flow pattern that is consistent with the scoring criteria. In some embodiments, the facility analyzes the blood flow pattern to automatically score the blood flow pattern in accordance with the scoring criteria.

Finally, the facility combines the scores assigned to the stages to determine an overall protocol grade for the patient, such as: no or minimal venous congestion; mild venous congestion; or severe venous congestion. In various embodiments, the facility displays this grade, causes it to be electronically communicated to a caregiver or the patient, causes it to be stored in an electronic health record for the patient, uses it as a basis for triggering one or more additional ultrasound studies, or radiological studies of other forms, etc.

By operating in some or all of the ways described above, the facility speeds the process of collecting ultrasound data used in a diagnostic protocol and making clinical diagnoses. Its automatic identification and analysis of visual features saves the physician time from manually searching for and evaluating these features. The facility's evaluation of a protocol's clinical decision tree provides a faster, more transparent, and more accurate way of suggesting clinical diagnoses.

Additionally, the facility improves the functioning of computer or other hardware, such as by reducing the dynamic display area, processing, storage, and/or data transmission resources needed to perform a certain task, thereby enabling the task to be permitted by less capable, capacious, and/or expensive hardware devices, and/or be performed with lesser latency, and/or preserving more of the conserved resources for use in performing other tasks. For example, by maximizing the usability of ultrasound images by more frequently identifying the important structures visualized therein, the facility avoids many cases in which re-imaging is required. By reducing the need to reimage, the facility consumes, overall, less memory and processing resources to capture additional images and perform additional rounds of automatic structure identification. Also, by reducing the amount of time needed to successfully complete a single diagnostic session, the facility permits an organization performing ultrasound imaging to purchase fewer copies of an ultrasound apparatus to serve the same number of patients, or operate an unreduced number of copies at a lower utilization rate, which can extend their useful lifespan, improves their operational status at every time in their lifespan, reduces the need for intra-lifespan servicing and calibration, etc.

FIG. 1 is a schematic illustration of a physiological sensing device 10, in accordance with one or more embodiments of the present disclosure. The device includes a probe 12 that, in the illustrated embodiment, is electrically coupled to a handheld computing device 14 by a cable 17. The cable 17 includes a connector 18 that detachably connects the probe 12 to the computing device 14. The handheld computing device 14 may be any portable computing device having a display, such as a tablet computer, a smartphone, or the like. In some embodiments, the probe 12 need not be electrically coupled to the handheld computing device 14, but may operate independently of the handheld computing device 14, and the probe 12 may communicate with the handheld computing device 14 via a wireless communication channel.

The probe 12 is configured to transmit an ultrasound signal toward a target structure and to receive echo signals returning from the target structure in response to transmission of the ultrasound signal. The probe 12 includes an ultrasound sensor 20 that, in various embodiments, may include an array of transducer elements (e.g., a transducer array) capable of transmitting an ultrasound signal and receiving subsequent echo signals.

The device 10 further includes processing circuitry and driving circuitry. In part, the processing circuitry controls the transmission of the ultrasound signal from the ultrasound sensor 20. The driving circuitry is operatively coupled to the ultrasound sensor 20 for driving the transmission of the ultrasound signal, e.g., in response to a control signal received from the processing circuitry. The driving circuitry and processor circuitry may be included in one or both of the probe 12 and the handheld computing device 14. The device 10 also includes a power supply that provides power to the driving circuitry for transmission of the ultrasound signal, for example, in a pulsed wave or a continuous wave mode of operation.

The ultrasound sensor 20 of the probe 12 may include one or more transmit transducer elements that transmit the ultrasound signal and one or more receive transducer elements that receive echo signals returning from a target structure in response to transmission of the ultrasound signal. In some embodiments, some or all of the transducer elements of the ultrasound sensor 20 may act as transmit transducer elements during a first period of time and as receive transducer elements during a second period of time that is different than the first period of time (i.e., the same transducer elements may be usable to transmit the ultrasound signal and to receive echo signals at different times).

The computing device 14 shown in FIG. 1 includes a display screen 22 and a user interface 24. The display screen 22 may be a display incorporating any type of display technology including, but not limited to, LCD or LED display technology. The display screen 22 is used to display one or more images generated from echo data obtained from the echo signals received in response to transmission of an ultrasound signal, and in some embodiments, the display screen 22 may be used to display color flow image information, for example, as may be provided in a Color Doppler imaging (CDI) mode. Moreover, in some embodiments, the display screen 22 may be used to display audio waveforms, such as waveforms representative of an acquired or conditioned auscultation signal.

In some embodiments, the display screen 22 may be a touch screen capable of receiving input from a user that touches the screen. In such embodiments, the user interface 24 may include a portion or the entire display screen 22, which is capable of receiving user input via touch. In some embodiments, the user interface 24 may include one or more buttons, knobs, switches, and the like, capable of receiving input from a user of the ultrasound device 10. In some embodiments, the user interface 24 may include a microphone 30 capable of receiving audible input, such as voice commands.

The computing device 14 may further include one or more audio speakers 28 that may be used to output acquired or conditioned auscultation signals, or audible representations of echo signals, blood flow during Doppler ultrasound imaging, or other features derived from operation of the device 10.

The probe 12 includes a housing, which forms an external portion of the probe 12. The housing includes a sensor portion located near a distal end of the housing, and a handle portion located between a proximal end and the distal end of the housing. The handle portion is proximally located with respect to the sensor portion.

The handle portion is a portion of the housing that is gripped by a user to hold, control, and manipulate the probe 12 during use. The handle portion may include gripping features, such as one or more detents, and in some embodiments, the handle portion may have a same general shape as portions of the housing that are distal to, or proximal to, the handle portion.

The housing surrounds internal electronic components and/or circuitry of the probe 12, including, for example, electronics such as driving circuitry, processing circuitry, oscillators, beamforming circuitry, filtering circuitry, and the like. The housing may be formed to surround or at least partially surround externally located portions of the probe 12, such as a sensing surface. The housing may be a sealed housing, such that moisture, liquid or other fluids are prevented from entering the housing. The housing may be formed of any suitable materials, and in some embodiments, the housing is formed of a plastic material. The housing may be formed of a single piece (e.g., a single material that is molded surrounding the internal components) or may be formed of two or more pieces (e.g., upper and lower halves) which are bonded or otherwise attached to one another.

In some embodiments, the probe 12 includes a motion sensor. The motion sensor is operable to sense a motion of the probe 12. The motion sensor is included in or on the probe 12 and may include, for example, one or more accelerometers, magnetometers, or gyroscopes for sensing motion of the probe 12. For example, the motion sensor may be or include any of a piezoelectric, piezoresistive, or capacitive accelerometer capable of sensing motion of the probe 12. In some embodiments, the motion sensor is a tri-axial motion sensor capable of sensing motion about any of three axes. In some embodiments, more than one motion sensor 16 is included in or on the probe 12. In some embodiments, the motion sensor includes at least one accelerometer and at least one gyroscope.

The motion sensor may be housed at least partially within the housing of the probe 12. In some embodiments, the motion sensor is positioned at or near the sensing surface of the probe 12. In some embodiments, the sensing surface is a surface which is operably brought into contact with a patient during an examination, such as for ultrasound imaging or auscultation sensing. The ultrasound sensor 20 and one or more auscultation sensors are positioned on, at, or near the sensing surface.

In some embodiments, the transducer array of the ultrasound sensor 20 is a one-dimensional (1D) array or a two-dimensional (2D) array of transducer elements. The transducer array may include piezoelectric ceramics, such as lead zirconate titanate (PZT), or may be based on microelectromechanical systems (MEMS). For example, in various embodiments, the ultrasound sensor 20 may include piezoelectric micromachined ultrasonic transducers (PMUT), which are microelectromechanical systems (MEMS)-based piezoelectric ultrasonic transducers, or the ultrasound sensor 20 may include capacitive micromachined ultrasound transducers (CMUT) in which the energy transduction is provided due to a change in capacitance.

The ultrasound sensor 20 may further include an ultrasound focusing lens, which may be positioned over the transducer array, and which may form a part of the sensing surface. The focusing lens may be any lens operable to focus a transmitted ultrasound beam from the transducer array toward a patient and/or to focus a reflected ultrasound beam from the patient to the transducer array. The ultrasound focusing lens may have a curved surface shape in some embodiments. The ultrasound focusing lens may have different shapes, depending on a desired application, e.g., a desired operating frequency, or the like. The ultrasound focusing lens may be formed of any suitable material, and in some embodiments, the ultrasound focusing lens is formed of a room-temperature-vulcanizing (RTV) rubber material.

In some embodiments, first and second membranes are positioned adjacent to opposite sides of the ultrasound sensor 20 and form a part of the sensing surface. The membranes may be formed of any suitable material, and in some embodiments, the membranes are formed of a room-temperature-vulcanizing (RTV) rubber material. In some embodiments, the membranes are formed of a same material as the ultrasound focusing lens.

Figure 2:
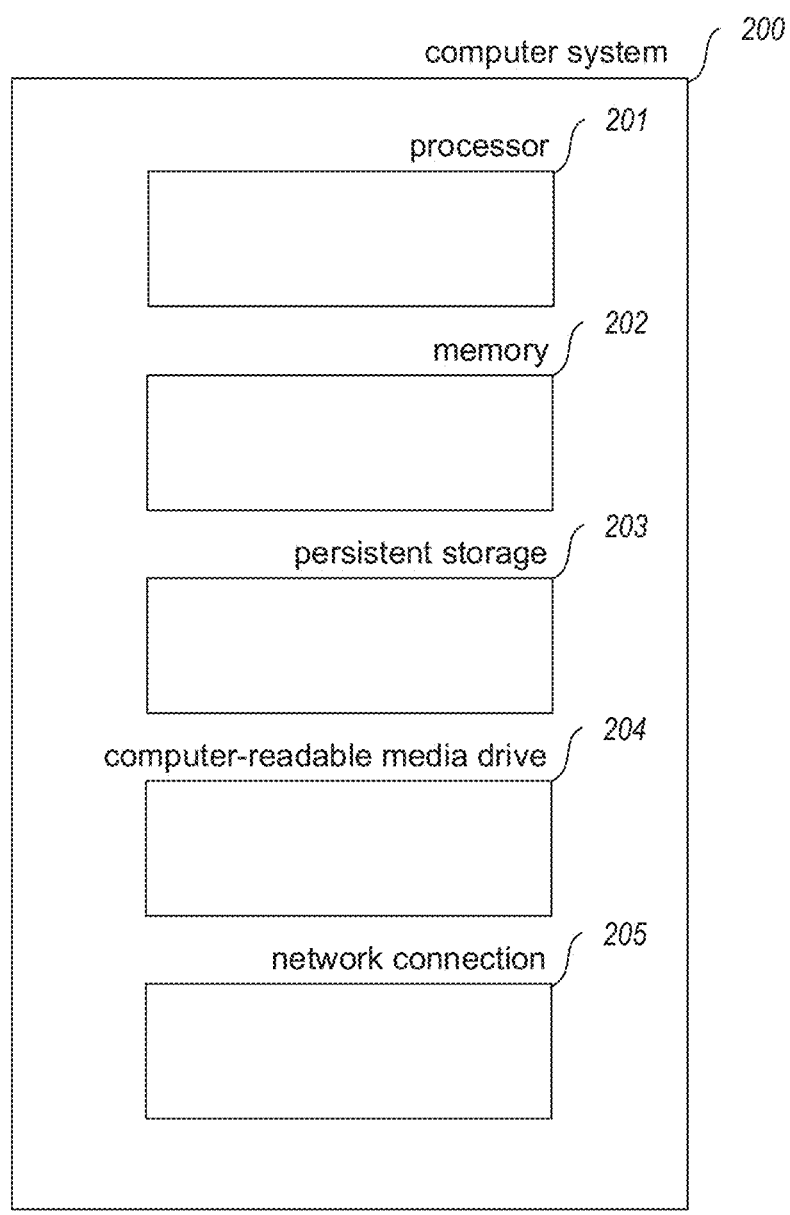
FIG. 2 is a block diagram showing some of the components typically incorporated in at least some of the computer systems and other devices on which the facility operates.

FIG. 2 is a block diagram showing some of the components typically incorporated in at least some of the computer systems and other devices on which the facility operates. In various embodiments, these computer systems and other devices 200 can include server computer systems, cloud computing platforms or virtual machines in other configurations, desktop computer systems, laptop computer systems, netbooks, mobile phones, personal digital assistants, televisions, cameras, automobile computers, electronic media players, etc. In various embodiments, the computer systems and devices include zero or more of each of the following: a processor 201 for executing computer programs and/or training or applying machine learning models, such as a CPU, GPU, TPU, NNP, FPGA, or ASIC; a computer memory 202 for storing programs and data while they are being used, including the facility and associated data, an operating system including a kernel, and device drivers; a persistent storage device 203, such as a hard drive or flash drive for persistently storing programs and data; a computer-readable media drive 204, such as a floppy, CD-ROM, or DVD drive, for reading programs and data stored on a computer-readable medium; and a network connection 205 for connecting the computer system to other computer systems to send and/or receive data, such as via the Internet or another network and its networking hardware, such as switches, routers, repeaters, electrical cables and optical fibers, light emitters and receivers, radio transmitters and receivers, and the like. While computer systems configured as described above are typically used to support the operation of the facility, those skilled in the art will appreciate that the facility may be implemented using devices of various types and configurations, and having various components.

Figure 3:
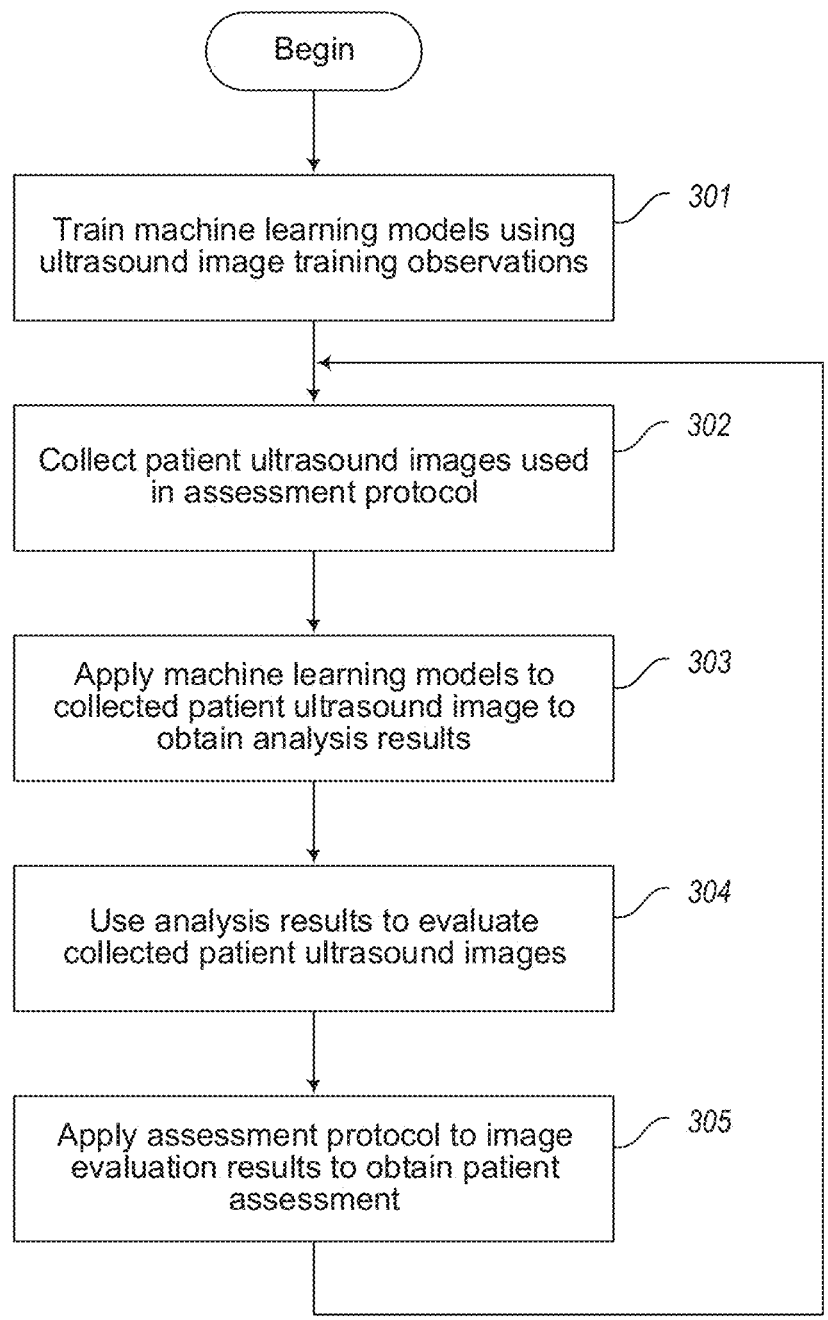
FIG. 3 is a flow diagram showing a process performed by the facility in some embodiments to perform an ultrasound diagnostic protocol such as VExUS.

FIG. 3 is a flow diagram showing a process performed by the facility in some embodiments to perform an ultrasound diagnostic protocol such as VExUS. In act 301, the facility trains one or more machine learning models—such as neural networks—using ultrasound image training observations. Particular models used by the facility in some embodiments are described below. Typical architectures for these are discussed below in connection with FIGS. 4 and 5.

In act 302, the facility collects ultrasound images and other ultrasound artifacts used in the assessment protocol. In some embodiments, the facility performs this collection by directly controlling an ultrasound machine. In some embodiments, the facility performs act 302 by presenting directions to a human user, which can include such details as ultrasound machine modes or settings to establish, ways of positioning or moving the probe, timing for capturing the artifact, etc. In various embodiments, the facility provides these directions in various modalities, including displaying them on the same display used to present captured ultrasound artifacts; displaying them on a separate display; presenting them in audio form based upon speech synthesis, recorded voice messages, etc.

In act 303, the facility applies machine learning models to the patient ultrasound images or other artifacts collected in act 302 to obtain analysis results. In some embodiments, the facility performs act 303 for each of a number of stages established by the assessment protocol, such as those described in greater detail below.

In act 304, the facility uses the analyses results produced in act 303 to evaluate the collected patient ultrasound images and other artifacts. In act 305, the facility applies the assessment protocol to the image evaluation results obtained in act 304 to obtain the patient assessment. In various embodiments, the facility outputs or stores the patient assessment on behalf of the patient, or takes or directs other kinds of actions in response. After act 305, the facility continues in act 302 to repeat this process for additional patients.

Those skilled in the art will appreciate that the acts shown in FIG. 3 and in each of the flow diagrams discussed below may be altered in a variety of ways. For example, the order of the acts may be rearranged; some acts may be performed in parallel; shown acts may be omitted, or other acts may be included; a shown act may be divided into subacts, or multiple shown acts may be combined into a single act, etc.

Figure 4:
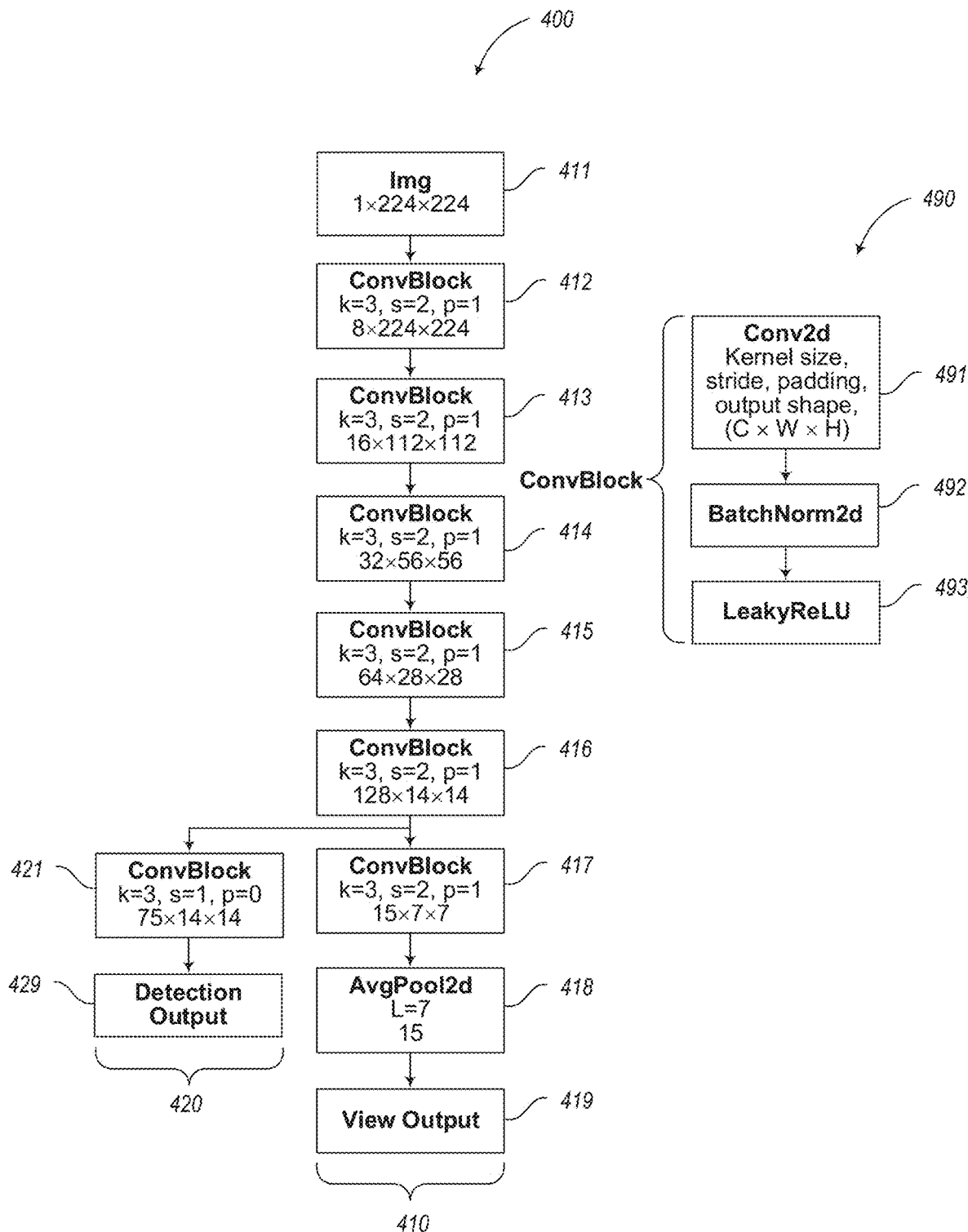
FIG. 4 is a model architecture diagram showing the organization of an object detection and view classification machine learning model used by the facility in some embodiments.
Figure 5:
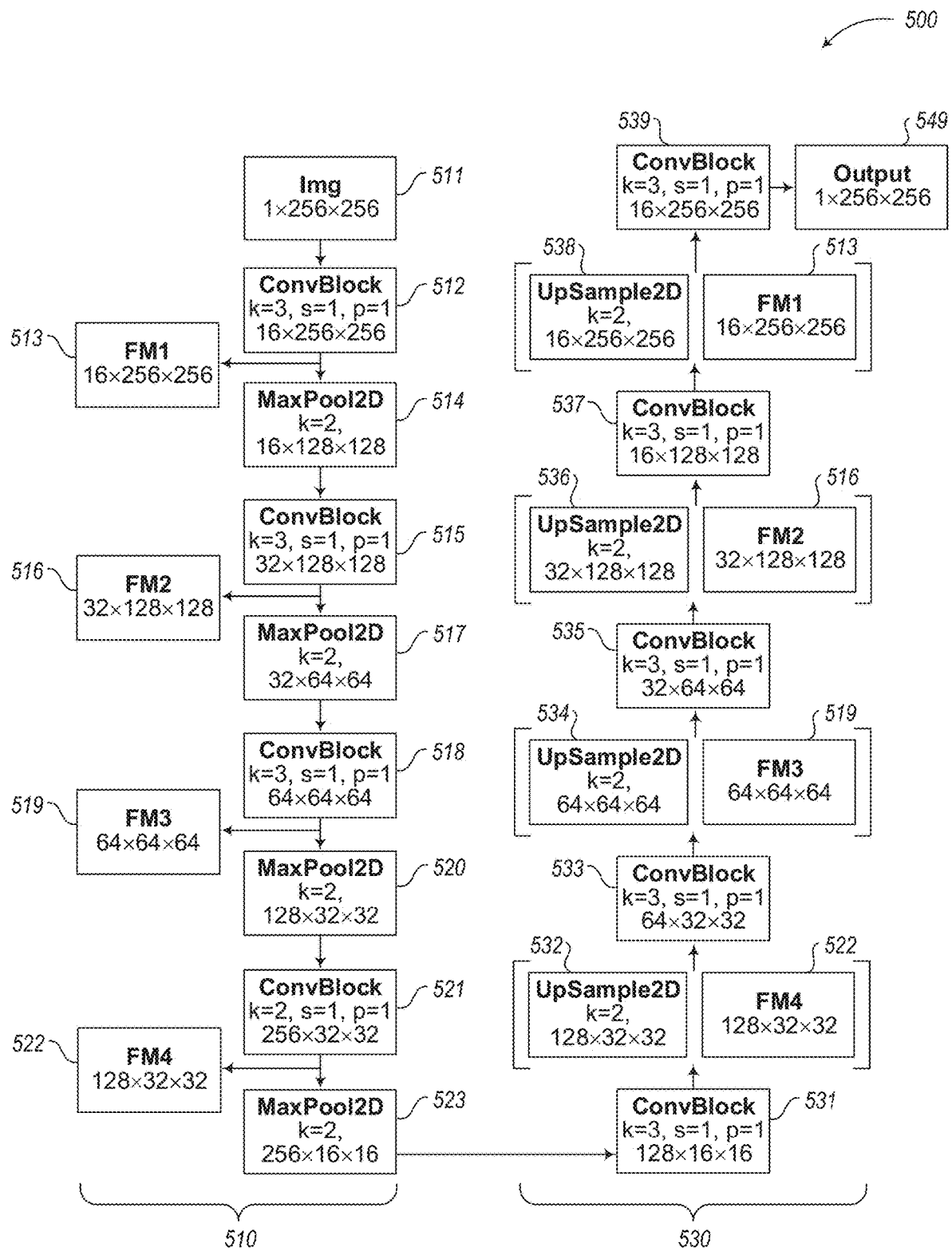
FIG. 5 is a model architecture diagram showing organization of a visual object segmentation/keypoint localization machine learning model used by the facility in some embodiments.

FIGS. 4 and 5 show typical architectures used by the facility for machine learning models that it employs. FIG. 4 is a model architecture diagram showing the organization of an object detection and view classification machine learning model used by the facility in some embodiments. A key or glossary 490 shows the composition of the ConvBlock structures shown in the architecture diagram 400. In particular, the glossary shows that a ConvBlock is made up of a convolutional layer 491, such as a 2D convolutional layer; a batch normalization layer 492, such as a 2D batch normalization layer; and a leaky ReLU activation function layer 493. The network includes convolutional blocks 412-417 and 421, specifying for each a kernel size k, a stride s, a padding output shape p and dimensions (channel×width×height). For example, the drawing shows that ConvBlock 412 has kernel size 3, stride 2, padding output shape 1, and dimensions 8×224×224. In addition to its convolutional blocks, the network includes two-dimensional average pool layer 418.

The network takes as its input an ultrasound image 411, such as a 1×224×224 greyscale ultrasound image. The network produces two outputs: a view output 419 that predicts the ultrasounds view from which the input image was captured, and a detection output port 129 that predicts the types of visual objects shown in the input ultrasound image.

Those skilled in the art will appreciate that a variety of neural network types and particular architectures may be straightforwardly substituted for the architecture shown in FIG. 4, and in the additional architecture diagrams discussed below.

FIG. 5 is a model architecture diagram showing organization of a visual object segmentation/keypoint localization machine learning model used by the facility in some embodiments. The network, sometimes described as a U-Net, is made up of a downsampling pathway 510 and an upsampling pathway 530. The network includes convolutional blocks 512, 515, 518, 521, 531, 533, 535, 537, and 539. The network further includes two-dimensional MaxPool layers 514, 517, 520 and 523; two-dimensional UpSample layers 532, 534, 536, and 538; and feature map layers 513, 516, 519, and 522. In addition to the connection between layers 523 and 531, the pathways are linked by feature map layers 513, 516, 519, and 522. The network takes as its input an ultrasound image 511, and produces an output 549 that predicts the location of visual objects, such as keypoints.

Figure 6:
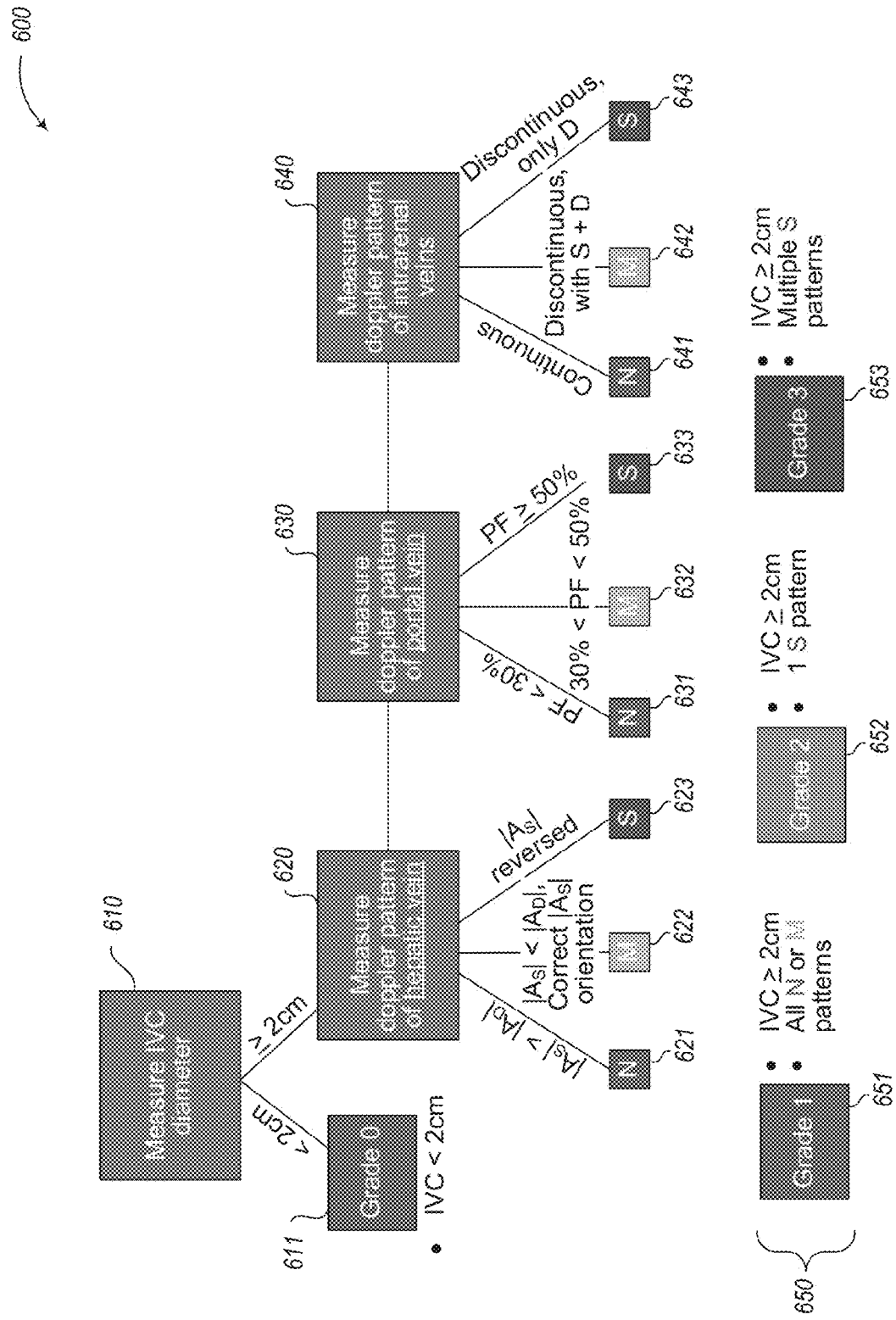
FIG. 6 is a protocol diagram showing a representation of the VExUS assessment protocol used by the facility in some embodiments.

FIG. 6 is a protocol diagram showing a representation of the VExUS assessment protocol used by the facility in some embodiments. A representation 600 of the protocol includes four stages 610, 620, 630, and 640, discussed at a high level in connection with FIG. 6 and in greater detail below. In stage 610, a facility measures the diameter of the IVC at a designated position along its length. If this measured diameter is smaller than two centimeters, then the facility assigns a grade 611 of zero, else the facility proceeds with stages 620, 630, and 640. In stage 620, a facility obtains a velocity versus time Doppler pattern for the patient's hepatic vein. In stage 620, if the Doppler pattern shows the amplitude of the systolic phase to be greater than the amplitude of the diastolic phase, then the facility assigns a score of N 621 to this stage; if the amplitude of the systolic phase is less than the amplitude of the diastolic phase, and the systolic phase has the correct orientation—hepatopetal flow, then the facility assigns the score of M 622; and if the systolic phase amplitude is reversed—hepatofugal, then the facility assigns a score of S 623 to the stage.

In stage 630, the facility obtains a Doppler pattern for the patient's portal vein. If the pulsatility fraction of the Doppler pattern—the fraction of the maximum velocity represented by the range of velocities—is less than 30%, then the facility assigns a score of N 631 to the stage; if this pulsatility fraction is between 30% and 50%, the facility assigns a score of M 632; and if the pulsatility fraction is 50% or larger, the facility assigns a score of S 633.

In stage 640, the facility obtains a Doppler pattern of the patient's intrarenal veins. If the Doppler pattern is continuous, then the facility assigns a score of N 641; if the pattern is discontinuous with systole and diastole, then the facility assigns a score of M 642; and if the pattern is discontinuous with only diastole, the facility assigns the score S 643.

After determining these scores, the facility uses them to determine a diagnostic grade 650 for the patient as follows: if the score for all of stages 620, 630, and 640 is either N or M, the facility assigns a grade 651 of 1; if the scores for these three stages contain a single S pattern, then the facility assigns a grade 652 of 2; and if two or more of the stages 620, 630, and 640 have S patterns, the facility assigns a grade 653 of 3.

Figure 7:
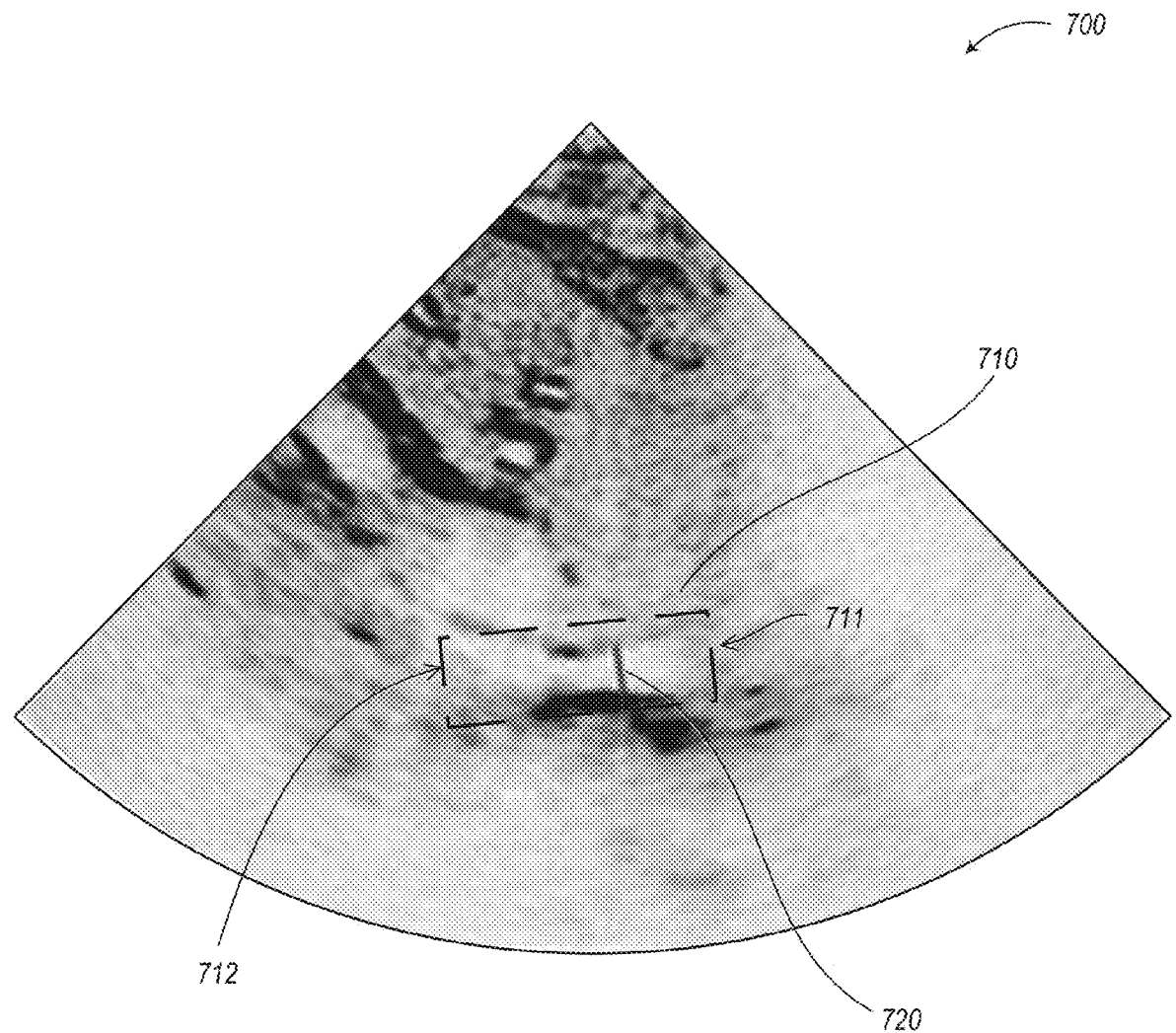
FIG. 7 is a sample ultrasound diagram illustrating the facility's performance of stage 610.

FIG. 7 is a sample ultrasound diagram illustrating the facility's performance of stage 610. While FIG. 6 shows the facility performing stage 610 first, in various embodiments, the facility performs the stages in various different orders. The ultrasound image 700 shows the patient's IVC 710. (This ultrasound image has been black-white inverted for legibility purposes, as have the additional ultrasound images discussed below). In some embodiments, before further analyzing this ultrasound image, the facility subjects it to a trained image grading machine learning model to assess the quality of the image for the purpose of the analysis, such as to ensure that it's possible to locate the walls of the IVC in the image, and determine its orientation. If the assessed quality level of the image is assessed to be inadequate, the facility automatically captures or directs the operator to capture a new image of the IVC. Otherwise, the facility applies a trained keypoint detection machine learning model to measure the inner diameter of the IVC at a prescribed point in the length of the IVC, such as two centimeters distal from hepatic vein junction 711. The facility proceeds to apply the decision making logic described above in connection with stage 610 to this distance.

Figure 8:
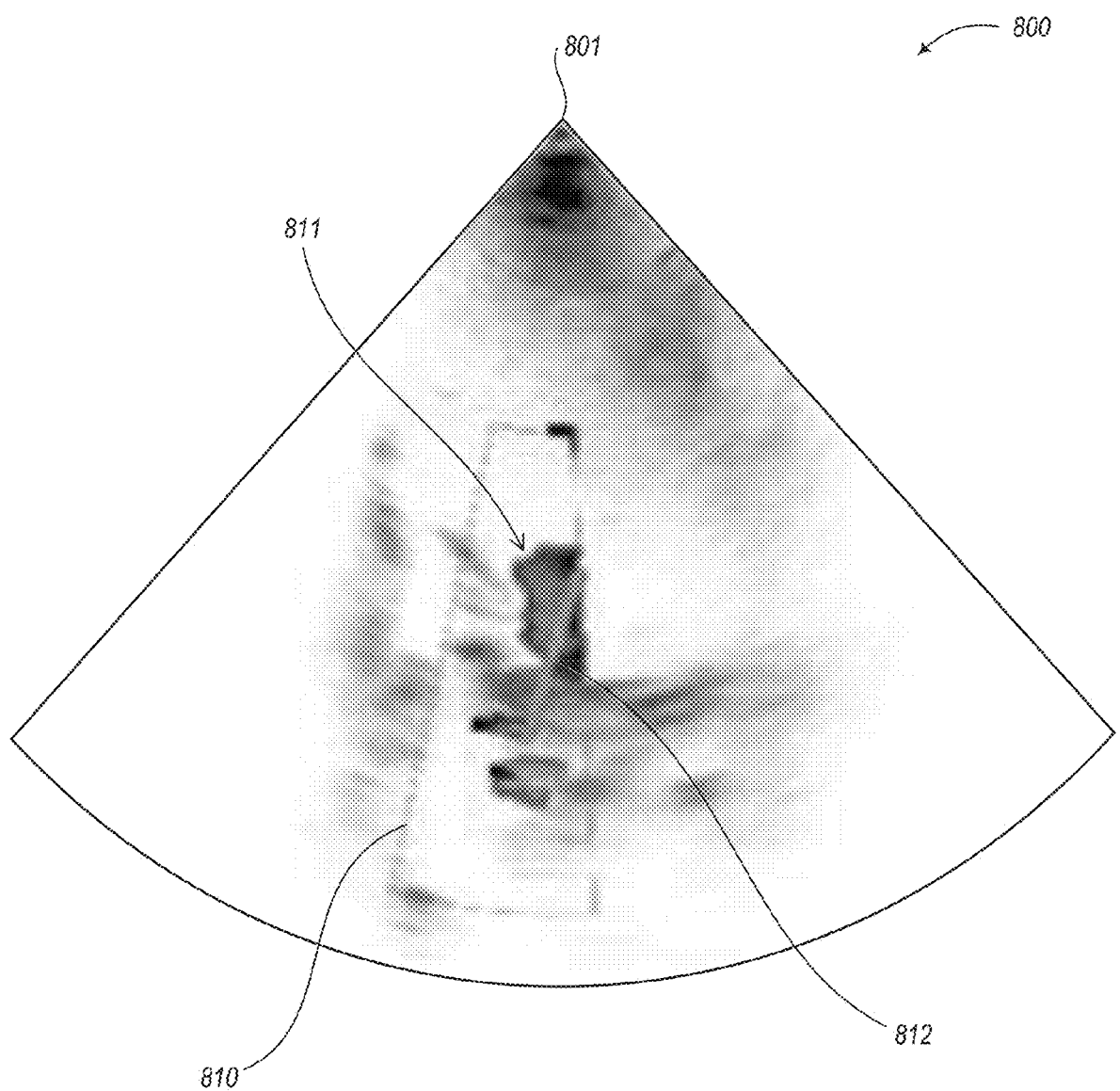
FIG. 8 is a sample ultrasound image illustrating the facility's performance of stage 620.

FIG. 8 is a sample ultrasound image illustrating the facility's performance of stage 620. The ultrasound image 800 shows the HV 811. In some embodiments, the facility assesses the quality of this ultrasound image before proceeding with further analysis. Were the images of adequate quality, the facility initializes a Doppler region of interest 810 that surrounds the HV. The facility invokes CW Doppler mode with respect to this region of interest to obtain a Doppler pattern for the HV. In some embodiments, the facility also determines the angular orientation of blood flow relative to a line defined by the origin 801 and the center of the HV blood flow; in these embodiments, the facility uses this angle to correct the velocity amplitude of the obtained Doppler pattern by dividing the velocity measured along the Doppler line by the cosine of this angle to estimate velocity along the direction of blood flow.

Figure 9:
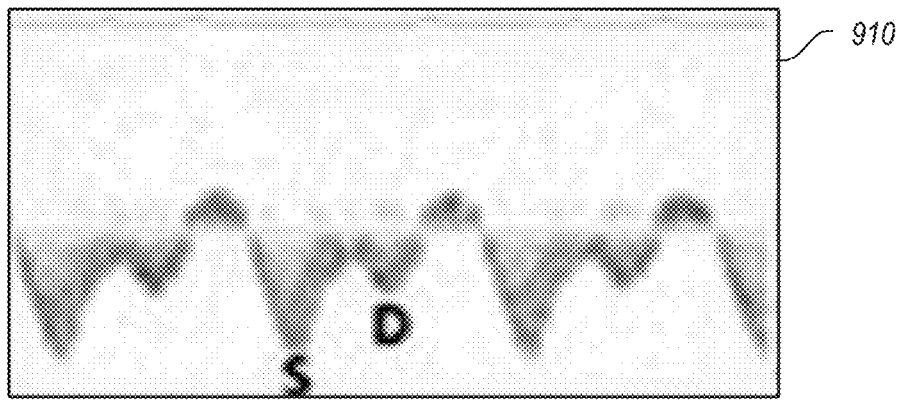
FIG. 9 is a Doppler pattern diagram showing sample Doppler patterns produced and analyzed by the facility in stage 620.
Figure 9:
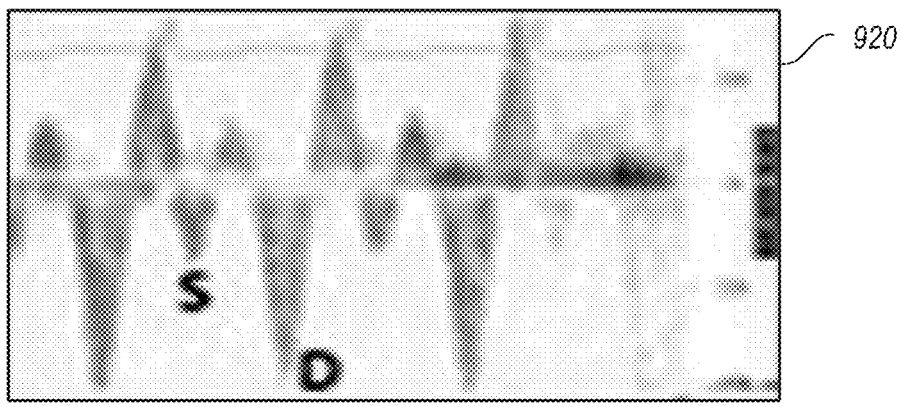
Figure 9:
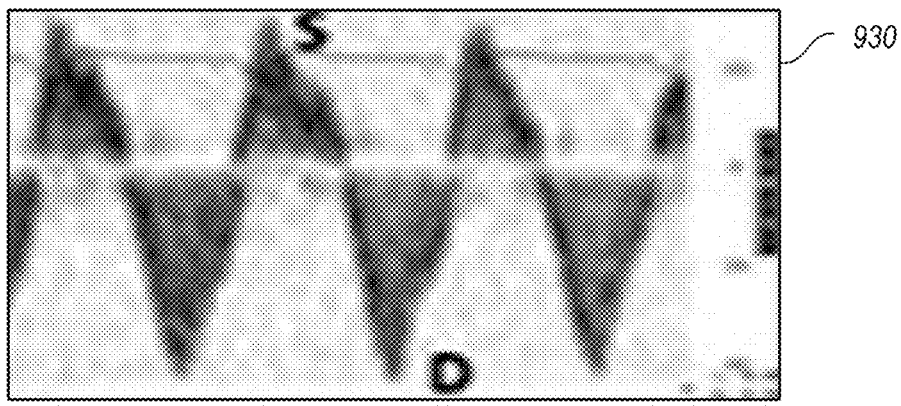

FIG. 9 is a Doppler pattern diagram showing sample Doppler patterns produced and analyzed by the facility in stage 620. In various embodiments, the facility uses various approaches to compare the amplitude of systolic phases to that of diastolic phases, and determine whether hepatopetal or hepatofugal flow is present, including asking the operator or other person present to make this assessment; performing this analysis using procedural programming; applying a trained machine learning model to predict the results of this analysis; etc. A Doppler pattern 910 obtained from a first patient shows a systolic phase—marked S—whose amplitude exceeds that of a corresponding diastolic phase—marked D. Accordingly, the facility scores the first patient N for stage 620. A Doppler pattern 920 is obtained by the facility for a second patient. In this pattern, the amplitude of a systolic phase S is less than the amplitude of a diastolic phase D, and hepatopetal flow is present; accordingly, the facility assigns this patient a grade of M for this stage. A Doppler pattern 930 is obtained by the facility for a third patient. This pattern shows hepatofugal flow; thus, the facility assigns a grade of S to stage 620 for this patient.

Figure 10:
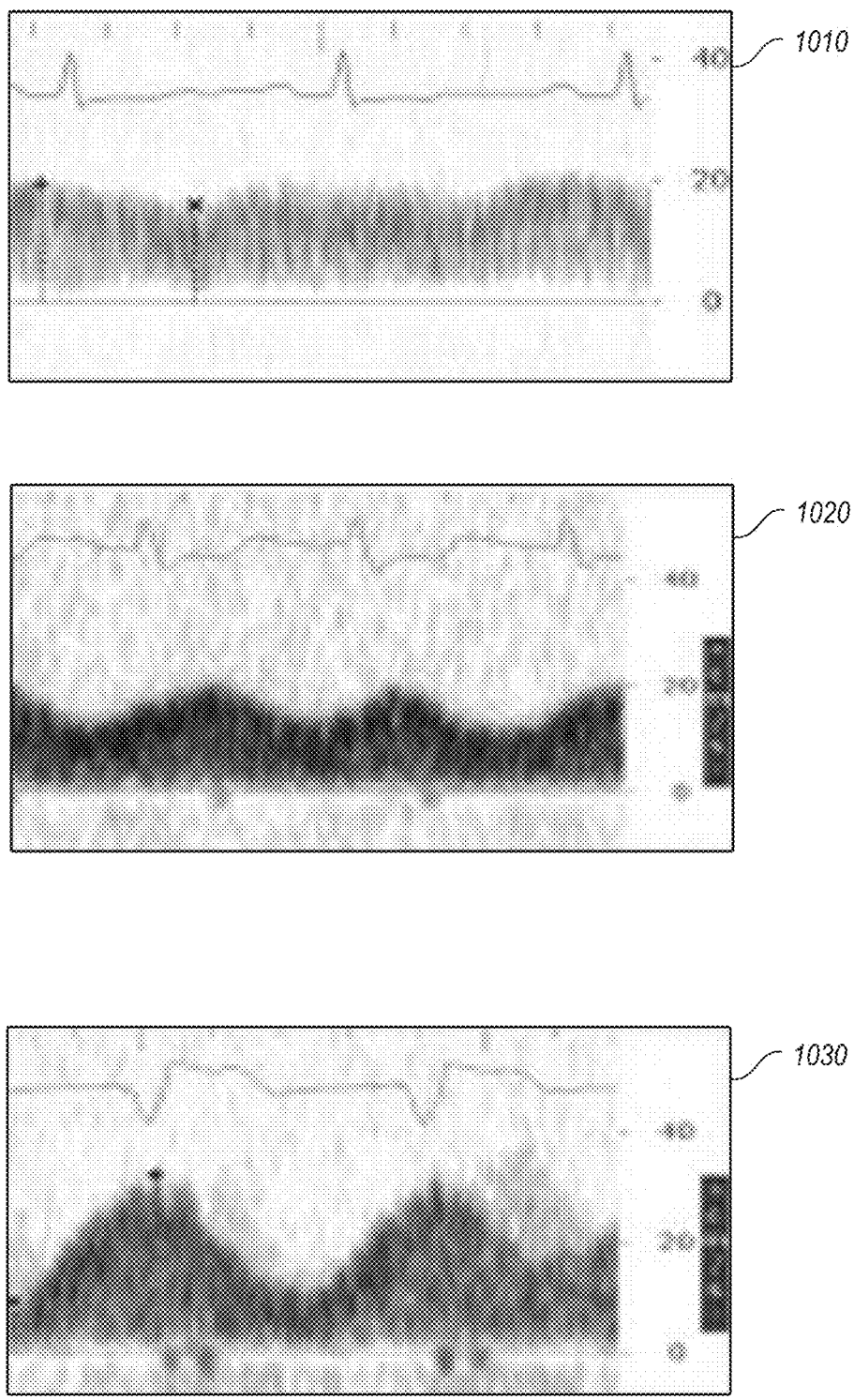
FIG. 10 is a Doppler pattern diagram showing sample Doppler patterns illustrating the facility's performance of stage 630.

FIG. 10 is a Doppler pattern diagram showing sample Doppler patterns illustrating the facility's performance of stage 630. These Doppler patterns are produced by using the object detection model to localize the center of the PV in an ultrasound image of it, establishing a Doppler region of interest around the center, and invoking CW Doppler mode. In some embodiments, the facility also determines the angular orientation of blood flow relative to a line defined by the origin 801 and the center of the PV blood flow; in these embodiments, the facility uses this angle to correct the velocity amplitude of the obtained Doppler pattern by dividing the velocity measured along the Doppler line by the cosine of this angle to estimate velocity along the direction of blood flow. In various embodiments, the facility determines pulsatility fraction from the resulting Doppler pattern in a variety of ways, including displaying the Doppler pattern and asking the operator or other person present to determine pulsatility fraction; using procedural programming, database functions, or spreadsheet operations to determine minimum and maximum velocities from a tabular representation of the Doppler pattern and apply the needed mathematical operations; applying a trained machine learning model to the Doppler pattern in either tabular or image form to predict pulsatility fraction; etc. One Doppler pattern 1010 is obtained by the facility for a fourth patient. In it, the pulsatility fraction—the fraction of the maximum velocity represented by the range of velocities—is less than 30%, and so the facility assigns a score of N for this stage to this patient. Doppler pattern 1020 is obtained by the facility for a fifth patient; in it, the pulsatility fraction is between 30% and 50%, and thus facility establishes a score of M for the fifth patient for this stage. Doppler pattern 1030 is obtained by the facility for a sixth patient; because it shows a pulsatility fraction above 50%, the facility assigns a score of S to the sixth patient for this stage.

Figure 11:
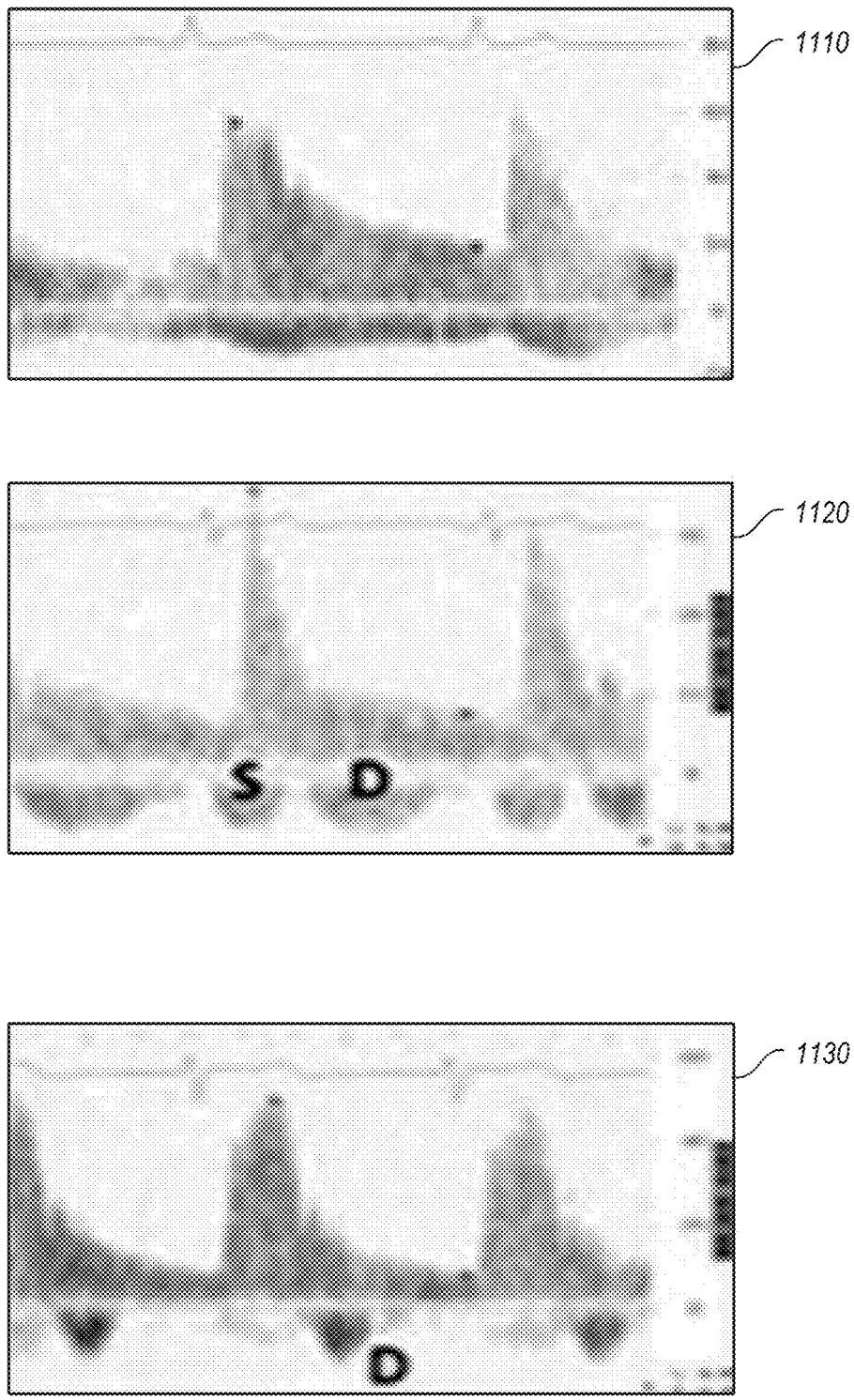
FIG. 11 is a Doppler pattern diagram showing sample Doppler patterns illustrating the facility's performance of stage 640.

FIG. 11 is a Doppler pattern diagram showing sample Doppler patterns illustrating the facility's performance of stage 640. For this stage, the facility obtains an ultrasound image of the patient's IRV, establishes a region of interest around the IRV, and invokes CW Doppler mode. In various embodiments, the facility uses various approaches to determine continuousness/discontinuousness and systole and diastole presence within the Doppler pattern, such as asking the user or another person present to make these determinations; applying procedural programming to do this analysis; or applying a trained machine learning model to perform this analysis. Doppler pattern 1110 is obtained by the facility for a seventh patient. Because it shows a continuous pattern, the facility scores the seventh patient normal for this stage. The facility obtains Doppler pattern 1120 for an eighth patient. Because this pattern is discontinuous with systole and diastole—marked S and D—the facility scores the eighth patient M for this stage. The facility obtains Doppler pattern 1130 for a ninth patient. Because it is discontinuous, with diastole but not systole, the facility grades the ninth patient S for this stage.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A system, comprising:
an ultrasound sensing device; and
a computing device, the computing device comprising:
a communication interface configured to directly receive ultrasound echo data sensed by the ultrasound sensing device from a patient, the received ultrasound echo data comprising a set of ultrasound artifacts, the set of ultrasound artifacts comprising one or more ultrasound images;
a memory configured to:
store a representation of a diagnostic protocol predicting a tentative diagnosis for a patient based on results of analyzing each of the ultrasound artifacts of the set, and
store one or more neural networks each trained to analyze one or more of the ultrasound artifacts of the set;
a processor configured to:
apply to each received ultrasound artifact at least one of the one or more trained neural networks to obtain an analysis result for the ultrasound artifact, and
scoring the diagnostic protocol using analysis results obtained for the ultrasound artifacts of the set to obtain a tentative diagnosis of the person; and
a display device configured to:
cause the tentative diagnosis of the person to be displayed.

2. The system of claim 1 wherein the ultrasound sensing device comprises a transducer.

3. The system of claim 1 wherein the ultrasound artifacts of the set each relate to a vein, and wherein the tentative diagnosis is a tentative diagnosis of venous congestion.

4. The system of claim 1 wherein the diagnostic protocol is the VExUS diagnostic protocol.

5. The system of claim 1 wherein a distinguished one of the trained neural networks is applied to a distinguished one of the set ultrasound artifacts, the distinguished ultrasound artifact comprising an ultrasound image showing a distinguished blood vessel, the application of the distinguished trained neural network to the distinguished ultrasound artifact identifying points on opposite walls of the distinguished blood vessel whose separation distance represents the internal diameter of the distinguished blood vessel.

6. The system of claim 1 wherein a first one of the trained neural networks is applied to a distinguished one of the set ultrasound artifacts, the distinguished ultrasound artifact comprising a first ultrasound image showing a distinguished blood vessel, the application of the first trained neural network to the distinguished ultrasound artifact identifying a point near the center of the distinguished blood vessel, the processor further being configured to initiate a CW Doppler capture using a region of interest defined to contain the identified point to obtain a CW Doppler pattern representing blood flow velocity over time used to produce the analysis result.

7. The system of claim 6, the processor further being configured to perform statistical analysis of the CW Doppler pattern to produce the analysis result.

8. The system of claim 6 wherein the statistical analysis of the CW Doppler pattern is performed by applying a second first one of the trained neural networks to the CW Doppler pattern.

9. The system of claim 6, the processor further being configured to perform continuity analysis of the CW Doppler pattern to produce the analysis result.

10. The system of claim 9 wherein the continuity analysis of the CW Doppler pattern is performed by applying a second first one of the trained neural networks to the CW Doppler pattern.

11. The system of claim 1 wherein a distinguished one of the trained neural networks is applied to a distinguished one of the set ultrasound artifacts, the distinguished ultrasound artifact comprising a first ultrasound image showing a subject anatomical feature, the application of the first trained neural network to the distinguished ultrasound artifact determining whether the distinguished ultrasound artifact shows the subject anatomical feature at a sufficiently high level of quality.

12. One or more instances of computer-readable media collectively having contents configured to cause a computing system to perform a diagnostic method with respect to a person, the method comprising:
accessing a set of trained machine learning models;
for each of a plurality of stages of a diagnostic ultrasound protocol for blood vessels:
causing an ultrasound device to capture from the person an ultrasound artifact of a type specified for the stage that features a blood vessel specified for the stage, the ultrasound artifact comprising an ultrasound image;
applying one of the trained machine learning models to the captured ultrasound artifact to produce a prediction;
determining a score for the stage based at least in part on the produced prediction; and
combining the determined scores to produce a diagnosis grade for the person.

13. The one or more instances of computer-readable media of claim 12, the method further comprising:
causing the diagnosis grade to be displayed.

14. The one or more instances of computer-readable media collectively of claim 12, the method further comprising:
causing the diagnosis grade to be persistently stored.

15. The one or more instances of computer-readable media of claim 12, the method further comprising:
for each of the machine learning models of the set, training the machine learning model using ultrasound artifacts captured from a plurality of people.

16. The one or more instances of computer-readable media of claim 12 wherein a distinguished one of the trained machine learning models is applied to the ultrasound artifact captured for a distinguished stage among the plurality of stages, the ultrasound artifact captured for the distinguished stage comprising an ultrasound image showing the blood vessel specified for the distinguished stage, the application of the distinguished trained neural network to the ultrasound artifact captured for the distinguished stage identifying points on opposite walls of the shown blood vessel whose separation distance represents the internal diameter of the shown blood vessel.

17. The one or more instances of computer-readable media of claim 12 wherein a first one of the trained neural networks is applied to the ultrasound artifact captured for a distinguished stage among the plurality of stages, the ultrasound artifact captured for the distinguished stage comprising a first ultrasound image showing the blood vessel specified for the distinguished stage, the application of the first trained neural network to the ultrasound artifact captured for the distinguished stage identifying a point near the center of the distinguished blood vessel, the method further comprising initiating a CW Doppler capture using a region of interest defined to contain the identified point to obtain a CW Doppler pattern representing blood flow velocity over time used to produce the analysis result.

18. The one or more instances of computer-readable media of claim 17, the method further comprising performing statistical analysis of the CW Doppler pattern to produce the analysis result.

19. The one or more instances of computer-readable media of claim 17, the method further comprising performing continuity analysis of the CW Doppler pattern to produce the analysis result.

20. The one or more instances of computer-readable media of claim 12 wherein a distinguished one of the trained neural networks is applied to the ultrasound artifact captured for a distinguished stage among the plurality of stages, the ultrasound artifact captured for the distinguished stage comprising a first ultrasound image showing a subject anatomical feature, the application of the first trained neural network to the distinguished ultrasound artifact determining whether the distinguished ultrasound artifact shows the subject anatomical feature at a sufficiently high level of quality.

21. A diagnostic method performed by a computing system with respect to a person, the method comprising:

accessing a set of trained machine learning models;

for each of a plurality of stages of a diagnostic ultrasound protocol for blood vessels:

causing an ultrasound device to capture from the person an ultrasound artifact of a type specified for the stage that features a blood vessel specified for the stage, the ultrasound artifact comprising an ultrasound image;

applying one of the trained machine learning models to the captured ultrasound artifact to produce a prediction;

determining a score for the stage based at least in part on the produced prediction; and combining the determined scores to produce a diagnosis grade for the person.

22. The method of claim 21, the method further comprising:

causing the diagnosis grade to be displayed.

23. The method collectively of claim 21, the method further comprising:

causing the diagnosis grade to be persistently stored.

24. The method of claim 21, the method further comprising:

for each of the machine learning models of the set, training the machine learning model using ultrasound artifacts captured from a plurality of people.

25. The one or more instances of computer-readable media of claim 21 wherein a distinguished one of the trained machine learning models is applied to the ultrasound artifact captured for a distinguished stage among the plurality of stages, the ultrasound artifact captured for the distinguished stage comprising an ultrasound image showing the blood vessel specified for the distinguished stage, the application of the distinguished trained neural network to the ultrasound artifact captured for the distinguished stage identifying points on opposite walls of the shown blood vessel whose separation distance represents the internal diameter of the shown blood vessel.

26. The method of claim 21 wherein a first one of the trained neural networks is applied to the ultrasound artifact captured for a distinguished stage among the plurality of stages, the ultrasound artifact captured for the distinguished stage comprising a first ultrasound image showing the blood vessel specified for the distinguished stage, the application of the first trained neural network to the ultrasound artifact captured for the distinguished stage identifying a point near the center of the distinguished blood vessel, the method further comprising initiating a CW Doppler capture using a region of interest defined to contain the identified point to obtain a CW Doppler pattern representing blood flow velocity over time used to produce the analysis result.

27. The method of claim 26, the method further comprising performing statistical analysis of the CW Doppler pattern to produce the analysis result.

28. The method of claim 26, the method further comprising performing continuity analysis of the CW Doppler pattern to produce the analysis result.

29. The method of claim 21 wherein a distinguished one of the trained neural networks is applied to the ultrasound artifact captured for a distinguished stage among the plurality of stages, the ultrasound artifact captured for the distinguished stage comprising a first ultrasound image showing a subject anatomical feature, the application of the first trained neural network to the distinguished ultrasound artifact determining whether the distinguished ultrasound artifact shows the subject anatomical feature at a sufficiently high level of quality.

* * * * *